US009056922B2

(12) United States Patent
Bathgate et al.

(10) Patent No.: US 9,056,922 B2
(45) Date of Patent: Jun. 16, 2015

(54) CHIMERIC RELAXIN POLYPEPTIDES COMPRISING AN A AND B CHAIN DERIVED FROM DIFFERENT RELAXIN FAMILY PEPTIDES

(75) Inventors: Ross Alexander David Bathgate, Brunswick West (AU); Mohammed Akhter Hossain, Brunswick West (AU); Chrishan Surendran Samuel, Glen Waverley (AU); John Desmond Wade, Canterbury (AU); Geoffrey W Tregear, Hawthorn (AU)

(73) Assignee: HOWARD FLOREY INSTITUTE OF EXPERIMENTAL PHYSIOLOGY AND MEDICINE, Parkville, Victoria (AU)

( * ) Notice: Subject to any disclaimer, the term of this patent is extended or adjusted under 35 U.S.C. 154(b) by 1293 days.

(21) Appl. No.: 12/740,450

(22) PCT Filed: Oct. 30, 2008

(86) PCT No.: PCT/AU2008/001605
§ 371 (c)(1),
(2), (4) Date: Dec. 10, 2010

(87) PCT Pub. No.: WO2009/055854
PCT Pub. Date: May 7, 2009

(65) Prior Publication Data
US 2011/0092418 A1    Apr. 21, 2011

Related U.S. Application Data

(60) Provisional application No. 60/983,768, filed on Oct. 30, 2007.

(51) Int. Cl.
*A61K 38/00* (2006.01)
*C07K 14/64* (2006.01)

(52) U.S. Cl.
CPC ............. *C07K 14/64* (2013.01); *C07K 2317/30* (2013.01); *A61K 38/00* (2013.01)

(58) Field of Classification Search
None
See application file for complete search history.

(56) References Cited

FOREIGN PATENT DOCUMENTS

| WO | 2006026355 A2 | 3/2006 |
| WO | 2008094437 A2 | 8/2008 |
| WO | 2009055854 A1 | 5/2009 |

OTHER PUBLICATIONS van der Westhuizen et al., Drug Discovery Today, 13(15/16):640-651, Aug. 2008.*
Liu et al., Molecular Pharmacology, 67(1): 231-240, 2005.*
Büllesbach et al., J Biological Chemistry, 275(45):35276-35280, 2000.*
Uniprot Accession No. P04808, Integrated into UniProtKB/Swiss-Prot on Aug. 13, 1987.*
Uniprot Accession No. P04090, Integrated into UniProtKB/Swiss-Prot on Nov. 1, 1986.*
GenBank Accession No. NM_006911.3. Hudson et al., EMBO J. 3 (10): 2333-2339 , 1984.*
GenBank Accession No. NM_134441.2. Hudson et al., EMBO J. 3 (10): 2333-2339 , 1984.*
Supplementary European Search Report Based on European Application No. 08844906 Dated Oct. 7, 2010.
Gilchrist; "Targettalk—IBC Conference. Kinase and G Protein—Coupled Receptor Targets"; IDrugs: The Investigational Drugs Journal; Jun. 2005; pp. 479-482; vol. 8; No. 6.
Hossain, The A-chain of Human Relaxin Family Peptides Has Distinct Roles in the Binding and Activation of the Different Relaxin Family Peptide Receptors, Journal of Biological Chemistry, Jun. 20, 2008, pp. 17287-17297, vol. 283 (25).
Hossain, The Minimal Active Structur of Human Relaxin-2, Journal of Biological Chemistry, Oct. 28, 2011, pp. 37555-37565, vol. 286 (43).
Hossain, Chimeric relaxin peptides highlight the role of the A-chain in th function of H2 relaxin, Elsevier, 2012, pp. 102-106, 35.
Chan, Identification of Key Residues Essential for the Structural Fold and Receptor Selectivity within the A-chain of Human Gene-2 (H2) Relaxin, Journal of Biological Chemistry, Nov. 30, 2012, pp. 41152-41164, vol. 287 (49).
Liu, Probing the functional Domains of Relaxin-3 and the Creation of a Selective Antagonist for RXFP3/GPCR135 over Relaxin Receptor RXFP1/LGR7, Annals of the New York Academy of Sciences, 2009, pp. 31-37, vol. 1160.
Park, Regulation of Receptor Signaling by Relaxin A Chain Motifs, Journal of Biological Chemistry, Nov. 14, 2008, pp. 32099-32109, vol. 283 (46).
Tan Y.Y et al."Comparison of relaxin receptors in rat isolated atria and uterus by use of synthetic and native relaxin analogues" British Journal of Pharmacology (1998) 123 (4): 762-770.
Bathgate R.A.D. et al. "Relaxin-3: Improved Synthesis Strategy and Demonstration of Its High-Affinity Interaction with the Relaxin Receptor LGR7 Both In Vitro and In Vivo" biochemistry (2006) 45 (3): 1043-1053.
Liu C. et al. "Relaxin-3/Insulin-Like Peptide 5 Chimeric Peptide, a Selective Ligand for G Protein-Coupled Receptor (GPCR) 135 and GPCR 142 over Leucine-Rich Repeat-Containing G Protein-Coupled Receptor 7" Molecular Pharmacology (2005) 67 (1): 231-240.
Kuei C. et al. "R3(BΔ23-27)R/I5 Chimeric Peptide, a Selective Antagonist for GPCR135 and GPCR142 over Relaxin Receptor LGR7: In Vitro and In Vivo Characterization" Journal of Biological Chemistry (2007) 282 (35): 25425-25435, Published Aug. 31, 2007.
International Search Report: International Application No. PCT/AU2008/001605, Feb. 3, 2015.

(Continued)

*Primary Examiner* — Daniel E Kolker
*Assistant Examiner* — Stacey N MacFarlane
(74) *Attorney, Agent, or Firm* — Miles & Stockbridge, P.C.

(57) ABSTRACT

Provided herein are modified relaxin polypeptides wherein the B chain comprises the core amino acid sequence CGR-XXX-R-XX-I/V-XX-CG (SEQ ID NO:1), where X is any amino acid. Also provided are modified relaxin polypeptides comprising at least an A and a B chain, wherein the A and B chains are derived from different naturally occurring relaxins and wherein the B chain comprises the core amino acid sequence CGR-XXX-R-XX-I/V-XX-CG (SEQ ID NO:1), where X is any amino acid.

13 Claims, 7 Drawing Sheets

(56) References Cited

OTHER PUBLICATIONS

Patent Cooperation Treaty: Written Opinion of the International Searching Authority, Apr. 30, 2010.

Supplementary EP Search Report. European Patent 05791027. Sep. 26, 2008.

Patent Cooperation Treaty: Written Opinion of the International Preliminary Examining Authority, Apr. 30, 2010.

Patent Cooperation Treaty: International Preliminary Report on Patentability, Apr. 30, 2010.

* cited by examiner

Figure 1

RELAXIN B-CHAINS

| | |
|---|---|
| Human 2 | DSWMEEVIKLCGRELVRAQIAICGMSTWS |
| Gorilla 2 | DSWKDDVIKLCGRELVRAQIAICGMSTWS |
| Chimpanzee 2 | DSWMDEVIKLCGRELVRAQIAICGMSTLG |
| Orangutan 2 | DSWMDEVIKVCGRELVRVQIAICGMSTLD |
| Human 1 | KWKDDVIKLCGRELVRAQIAICGMSTWS |
| Gorilla 1 | KWKDDVIKLCGCELVRAQIAICGMSTWS |
| Chimpanzee 1 | DSWMDEVIKLCGRELVRAQIAICGKSTWS |
| Orangutan 1 | KWKEDVIKLCSRELVRTQIAICGMSTWR |

Figure 2

RELAXIN A-CHAINS

| | |
|---|---|
| Human 2 | ZLYSALANKCCHVGCTKRSLARFC |
| Gorilla 2 | ZLYSALANKCCHVGCTKRSLARFC |
| Chimpanzee 2 | ZLYSALANKCCHVGCTKRSLARFC |
| Orangutan 2 | ZLYSALANKCCHVGCTKRSLARFC |
| Human 1 | RPYVALFEKCCLIGCTKRSLAKYC |
| Gorilla 1 | RPYVALFEKCCLIGCTKRSKAKYC |
| Chimpanzee 1 | ZPYVALFEKCCLIGCTKRSLANYC |
| Orangutan 1 | PYMAVFEKCCLIGCTKRSLAKYC |

Figure 3
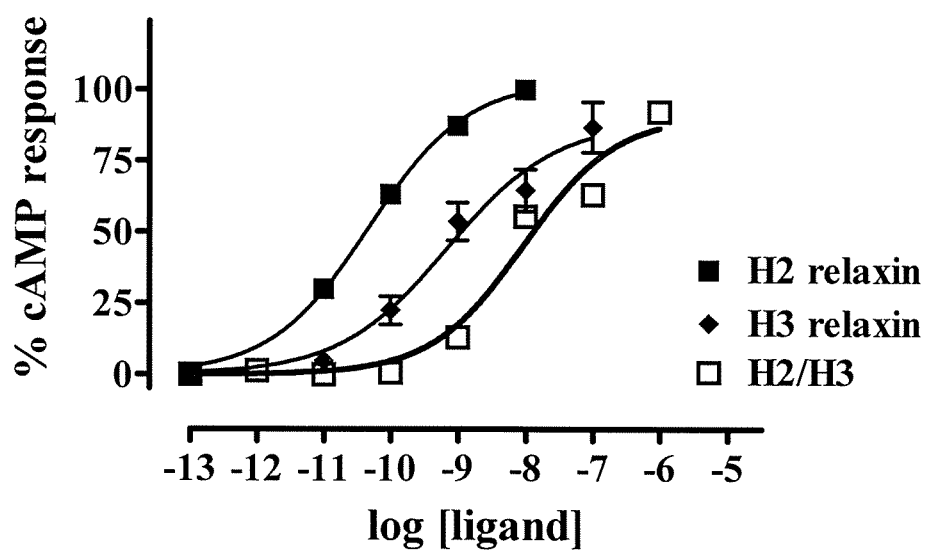
A
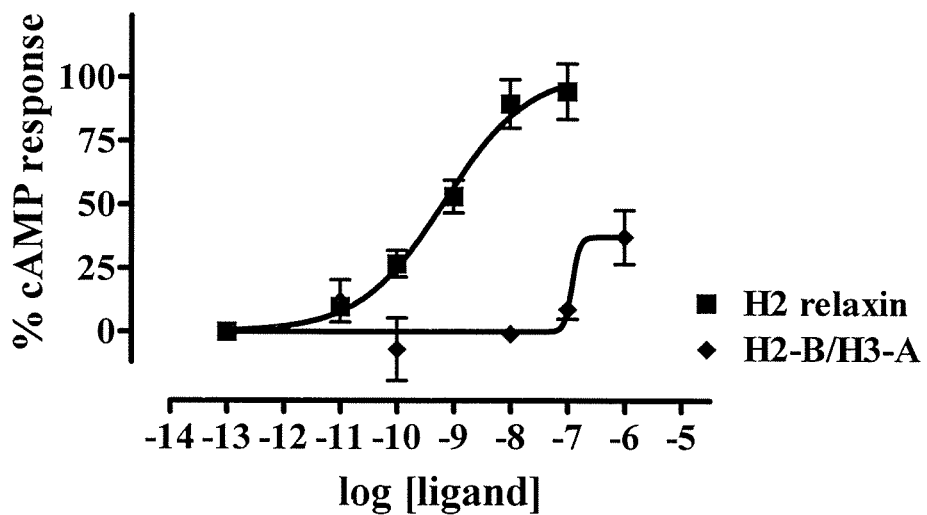
B

Figure 4
A
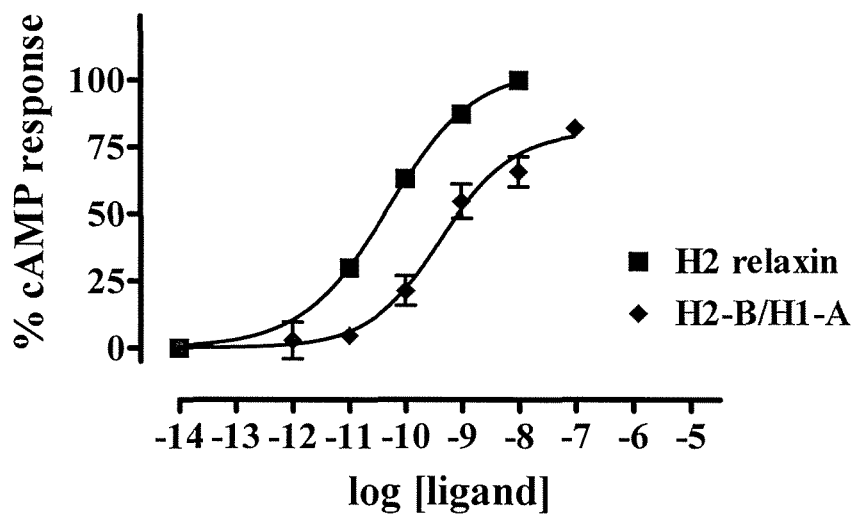
B
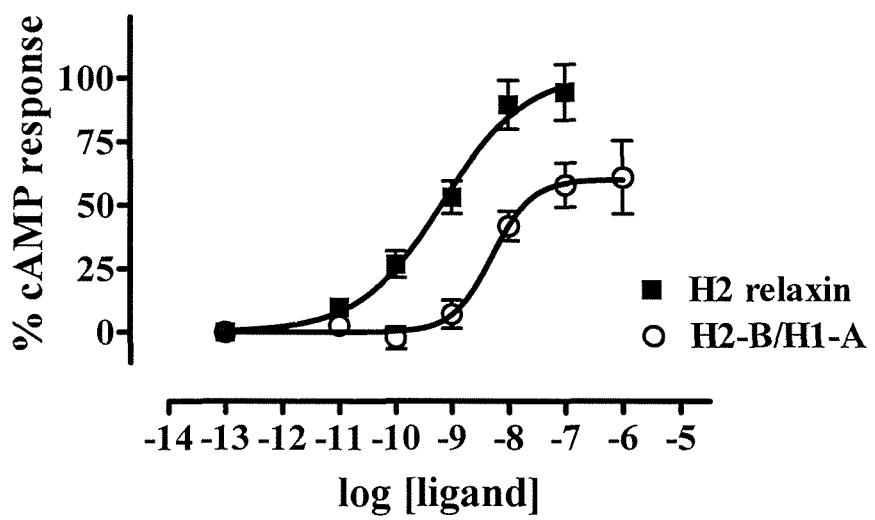

CHIMERIC RELAXIN POLYPEPTIDES COMPRISING AN A AND B CHAIN DERIVED FROM DIFFERENT RELAXIN FAMILY PEPTIDES

RELATED APPLICATIONS

This application is a §371 National Stage Application of PCT/AU2008/001605 filed Oct. 30, 2008, which claims priority to U.S. Application No. 60/983,768 filed Oct. 30, 2007.

FIELD OF THE INVENTION

The present invention relates generally to modified relaxin polypeptides, and to nucleic acids encoding the same. The present invention in particular relates to modified relaxin polypeptides which specifically bind to the LGR7 and/or LGR8 receptor and more particularly relates to chimeric polypeptides possessing a B chain derived from human relaxin 2 or human relaxin 1, or a modified form thereof. The invention also relates to uses of polypeptides of the invention, methods employing the same and to compositions comprising such polypeptides.

BACKGROUND OF THE INVENTION

Relaxin is a heterodimeric peptide hormone composed, in its mature form, of an A chain and a B chain linked via a disulphide bridge. Relaxin is produced as a prohormone with a third amino acid (C) chain in the configuration B-C-A. Relaxin is a member of a protein hormone superfamily which also includes insulin, insulin-like grown factors I and II (IGF-I and IGF-II), and the insulin-like hormones INSL3, 4, 5 and 6. The relaxin superfamily members have a wide range of biological activities which are well described in the art.

Relaxin has been conserved through vertebrate evolution and has been characterised in a large and diverse range of vertebrate species. In particular the cysteine residues in the B and A chains responsible for the intra- and inter-chain disulphide bonds are highly conserved. Whilst in most species only two forms of relaxin have been identified (relaxin and relaxin-3), in humans three distinct forms of relaxin have been described and the genes and polypeptides characterised. These have been designated H1, H2 and H3. Homologues of H1 and H2 relaxin have been identified in other higher primates including chimpanzees, gorillas and orangutans.

Of the three forms of relaxin in humans, the polypeptide encoded by the H2 gene is the major stored and circulating form. H2 relaxin is the only form known to be secreted in the blood. H1 relaxin expression is largely restricted to the decidua, placenta and prostate, whilst H3 relaxin expression is predominant in the brain. The differing expression patterns for H1, H2 and H3 relaxin may suggest some differences in biological roles, however all three forms display similar biological activity as determined, for example, by their ability to stimulate cAMP activity in cells expressing relaxin receptors, and accordingly share many biological functions in common.

The biological functions of relaxin include an ability to inhibit myometrial contractions, to stimulate remodelling of connective tissue and to induce softening of the tissues of the birth canal. Additionally, relaxin increases growth and differentiation of the mammary gland and nipple and induces the breakdown of collagen, one of the main components of connective tissue. Although originally identified as a pregnancy hormone, it is now well established that relaxin has a variety of other important roles and acts as an endocrine and paracrine factor in a broad range of tissues. For example, relaxin causes a widening of blood vessels (vasodilatation) in the kidney, mesocaecum, lung and peripheral vasculature, which leads to increased blood flow or perfusion rates in these tissues. It also stimulates an increase in heart rate and coronary blood flow, and increases both glomerular filtration rate and renal plasma flow. The brain is another target tissue for relaxin where it has been shown to bind to receptors in the circumventricular organs to affect numerous activities including blood pressure, drinking, memory related functions and addictive behaviours.

Aberrant relaxin activity and/or expression is also implicated in a number of disorders and diseases such as, for example, cardiovascular diseases, renal diseases, fibrotic disorders (including cardiac fibrosis and fibrosis associated with airway remodelling), neurological disorders, immune diseases and endometrial and reproductive disorders. According there exists a number of important clinical applications of relaxin and relaxin agonists and antagonists. The administration of recombinant relaxin has been demonstrated to be effective in reversing collagen deposition in pulmonary, renal and cardiac fibrosis (see for example, Samuel et al., 2004, *Endocrinology* 145:4125-4133; Mookerjee et al., 2005, *Ann NY Acad Sci* 1041:190-193; co-pending U.S. patent application Ser. No. 11/133,763).

The biological actions of relaxin are mediated through G protein coupled receptors (see Bathgate et al., 2006, *Pharmacol Rev* 58:7-31 for a review). To date, H1, H2 and H3 relaxins have been shown to primarily recognise and bind four receptors, LGR7 (RXFP1), LGR8 (RXFP2), GPCR135 (RXFP3) and GPCR142 (RXFP4). LGR7 is the most widely expressed of these receptors and binds each of H1, H2 and H3 with high affinity. H1 and H2 relaxin also bind LGR8. H3 relaxin binds GPCR135 and GPCR142 in addition to LGR7.

In view of the range of potential clinical applications of relaxin there is a continuing need for the development of novel polypeptides displaying relaxin activity, which polypeptides have improved or varied biological activity when compared to naturally occurring relaxin polypeptides and/or which display different receptor binding specificities to naturally occurring relaxin polypeptides.

SUMMARY OF THE INVENTION

The present invention provides novel modified polypeptides having relaxin activity, in particular which polypeptides are specific for the LGR7 (RXFP1) and/or LGR8 (RXFP2) receptors. Polypeptides of the invention are "modified" in that they possess different combinations of B and A chains than those present in naturally occurring relaxin polypeptides. Thus, the invention contemplates novel chimeric relaxin polypeptides. Typically the B chain of a modified polypeptide in accordance with an embodiment of the invention is derived from H2 relaxin or H1 relaxin or is a modified sequence comprising a core amino acid sequence common to the B chain of H2 and H1 relaxins.

According to one aspect of the invention there is provided a modified relaxin polypeptide wherein the B chain comprises the core amino acid sequence CGR-XXX-R-XX-I/V-XX-CG (SEQ ID NO:1) where X is any amino acid.

The B chain of the modified polypeptide may comprise the core amino acid sequence CGR-XXX-R-XX-I-XX-CG (SEQ ID NO:2) where X is any amino acid.

The B chain of the modified polypeptide may comprise the amino acid sequence KLCGRELVRAQIAIC (SEQ ID NO:3). The B chain of the modified polypeptide may comprise the amino acid sequence VIKLCGRELVRAQIA-ICGMSTWS (SEQ ID NO:4).

The B chain may comprise the amino acid sequence XWXXXVIKLCGRELVRAQIAICGMSTWS (SEQ ID NO:5), where X is any amino acid.

The B chain may comprise the amino acid sequence $X_1X_2WX_3X_4X_4$VIKLCGRELVRAQIAICGMSTWS (SEQ ID NO:6) where: $X_1$ (if present) is D; $X_2$ is S or K; $X_3$ is M or K; and $X_4$ is an acidic residue. In one embodiment, $X_4$ is D or E.

In one embodiment the modified polypeptide comprises the H2 relaxin B chain sequence DSWMEEVIKLCGRELVRAQIAICGMSTWS (SEQ ID NO:7) or a portion or variant thereof. In another embodiment the modified polypeptide comprises the H1 relaxin B chain sequence KWKDDVIKLCGRELVRAQIAICGMSTWS (SEQ ID NO:8) or a portion or variant thereof.

In one embodiment, the B chain sequence is modified from that found in H2 or H1 relaxin. For example, the B chain sequence may be truncated or possess amino acid substitutions or modifications when compared with either the H2 or H1 relaxin B chain. Thus, the B chain may be modified by one or more amino acid insertions, deletions and/or substitutions.

The amino acid sequence of the A chain of the modified polypeptide may be derived from, for example, relaxin 1, relaxin 2, relaxin 3, insulin, IGF-I, IGF-II or insulin-like peptides (INSL) 3, 4, 5 or 6, with the proviso that when the B chain sequence is derived from H2 relaxin the A chain sequence is not derived from H2 relaxin and when the B chain sequence is derived from H1 relaxin the A chain sequence is not derived from H1 relaxin. The A chain sequence may be derived from a human or non-human relaxin or relaxin superfamily polypeptide. Where the A chain is derived from a human polypeptide, the A chain may comprise an amino acid sequence as set forth in any one of SEQ ID Nos: 9 to 18, or a portion thereof. Alternatively, the A chain amino acid sequence of the modified polypeptide may itself be modified, for example as described herein for the B chain.

According to a second aspect of the invention there is provided a modified relaxin polypeptide comprising at least an A and a B chain, wherein the A and B chains are derived from different naturally occurring relaxins and wherein the B chain comprises the core amino acid sequence CGR-XXX-R-XX-I/V-XX-CG (SEQ ID NO:1) where X is any amino acid.

In a third aspect the invention provides a modified relaxin polypeptide comprising a B chain, or portion thereof, derived from relaxin 2 and an A chain, or portion thereof, derived from one of relaxin 1, relaxin 3, insulin, IGF-I, IGF-II, INSL3, INSL4, INSL5 and INSL6.

In a fourth aspect the invention provides a polynucleotide encoding a modified polypeptide of the first, second or third aspect.

In a fifth aspect the present invention provides a pharmaceutical composition comprising a modified polypeptide of the first, second or third aspect or a polynucleotide of the fourth aspect, optionally together with one or more pharmaceutically acceptable carriers, excipients or diluents.

In a sixth aspect the present invention provides a method for treating or preventing a disorder associated with aberrant expression or activity of relaxin, the method comprising administering to a subject in need thereof a modified polypeptide of the first, second or third aspect, a polynucleotide of the fourth aspect or a pharmaceutical composition of the fifth aspect.

In a seventh aspect the present invention provides the use of a modified polypeptide of the first, second or third aspect, or a polynucleotide of the fourth aspect for the manufacture of a medicament for the treatment or prevention of a disorder associated with aberrant expression or activity of relaxin.

BRIEF DESCRIPTION OF THE DRAWINGS

The present invention will now be described, by way of non-limiting example only, with reference to the accompanying drawings.

FIG. 1. Alignment of primate relaxin B chain sequences. Conserved amino acid residues are underlined.

FIG. 2. Alignment of primate relaxin A chain sequences. Conserved amino acid residues are underlined.

FIG. 3. Stimulation of cAMP by human relaxin 2 (H2) (filled squares), human relaxin 3 (H3) (diamonds) and a modified polypeptide of the invention comprising the H2 B chain and the H3 A chain (open squares) in cells expressing (A) the LGR7 (RXFP1) receptor or (B) the LGR8 (RXFP2) receptor.

FIG. 4. Stimulation of cAMP in cells expressing (A) the LGR7 (RXFP1) receptor or (B) the LGR8 (RXFP2) receptor, by human relaxin 2 (H2) (filled squares) and a modified polypeptide of the invention comprising the H2 B chain and the H1 A chain (diamonds in A; open circles in B).

DETAILED DESCRIPTION OF THE INVENTION

Figure 5:
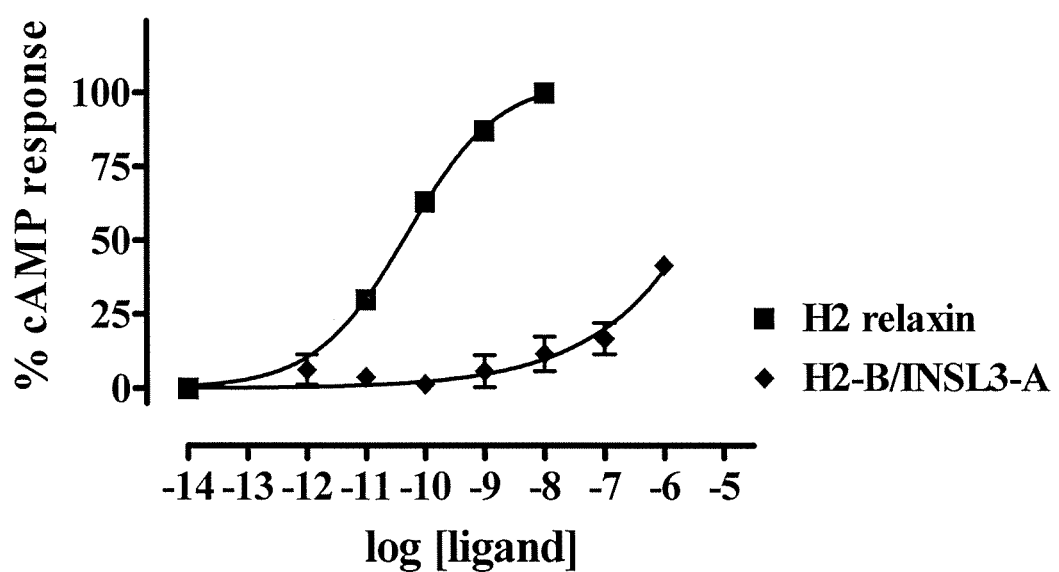
FIG. 5. Stimulation of cAMP by human relaxin 2 (H2) (filled squares) and a modified polypeptide of the invention comprising the H2 B chain and the INSL3 A chain (diamonds) in cells expressing the LGR7 (RXFP1) receptor.

Amino acid sequences of relaxin superfamily B chain and A chain sequences described herein are set forth in SEQ ID NOs.: 1 to 18. The sequences set forth in SEQ ID NOs.: 1 and 2 represent core 14 amino acid consensus sequences for the relaxin B chain. The sequence set forth in SEQ ID NO:3 represents a core 15 amino acid consensus sequence for the relaxin B chain. The sequence set forth in SEQ ID NO:4 represents a core 23 amino acid sequence common to the B chains of human relaxin 2 and human relaxin 1. The sequences set forth in SEQ ID NOs : 5 and 6 represent consensus sequences between the B chains of human relaxin 2 and human relaxin 1. The sequences set forth in SEQ ID Nos: 7 to 18 are derived from the corresponding human polypeptide sequences as follows: relaxin 2 B chain (SEQ ID NO:7); relaxin 1 B chain (SEQ ID NO:8); relaxin 2 A chain (SEQ ID NO:9); relaxin 1 A chain (SEQ ID NO:10); relaxin 3 A chain (SEQ ID NO:11); INSL3 A chain (SEQ ID NO:12); INSL4 A chain (SEQ ID NO:13); INSL5 A chain (SEQ ID NO:14); INSL6 A chain (SEQ ID NO:15); insulin A chain (SEQ ID NO:16); IGF-I A chain (SEQ ID NO:17); and IGF-II A chain (SEQ ID NO:18).

Throughout this specification and the claims which follow, unless the context requires otherwise, the word "comprise", and variations such as "comprises" or "comprising", will be understood to imply the inclusion of a stated integer or step or group of integers or steps but not the exclusion of any other integer or step or group of integers or steps.

The articles "a" and "an" are used herein to refer to one or to more than one (i.e., to at least one) of the grammatical object of the article. By way of example, "an element" means one element or more than one element.

The term "polypeptide" means a polymer made up of amino acids linked together by peptide bonds. The term "peptide" may also be used to refer to such a polymer although in some instances a peptide may be shorter (i.e. composed of fewer amino acid residues) than a polypeptide. Nevertheless, the terms "polypeptide" and "peptide" are used interchangeably herein.

The term "relaxin polypeptide" as used herein means a polypeptide, whether modified in accordance with the present invention or corresponding to a naturally occurring relaxin molecule which displays biological activity typically associated with relaxin. The level of such relaxin biological activity displayed by a modified polypeptide of the invention may be equivalent to that of a naturally occurring relaxin, or may be enhanced or reduced when compared with the activity of a naturally occurring relaxin.

The term "modified" as used herein in the context of a relaxin polypeptide means a polypeptide that differs from a naturally occurring relaxin polypeptide at one or more amino acid positions in one or more peptide chains of such naturally occurring polypeptide.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated. The terms "polynucleotide" and "nucleic acid" are used interchangeably herein.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution. The nature of other conservative amino acid substitutions are well known to those skilled in the art.

As used herein the term "derived" in the context of relaxin A and B chains in modified polypeptides means that the A and B chain sequences correspond to, originate from, or otherwise share significant sequence homology with naturally occurring A and B chain sequences. Thus, for example, a relaxin B chain present in a modified polypeptide may be identical to the B chain sequence of a relaxin from any species, such as the human H1 or H2 relaxin or may be a modified version or variant thereof. Alternatively, the B chain in a modified polypeptide may share sequence homology with one or more B chain sequences from any species. In the context of relaxin polypeptides the term "naturally occurring" refers to relaxin polypeptides as encoded by and produced from the genome of an organism. For example in humans three distinct forms of relaxin have been identified to date, H1, H2 and H3. Each of these forms is considered herein as a different "naturally occurring" relaxin.

As used herein the terms "treating", "treatment", "preventing" and "prevention" refer to any and all uses which remedy a condition or symptoms, prevent the establishment of a condition or disease, or otherwise prevent, hinder, retard, or reverse the progression of a condition or disease or other undesirable symptoms in any way whatsoever. Thus the terms "treating" and "preventing" and the like are to be considered in their broadest context. For example, treatment does not necessarily imply that a patient is treated until total recovery. Similarly, "prevention" dose not necessarily mean that the subject will not eventually contract a particular condition or disease. Rather, "prevention" encompasses reducing the severity of, or delaying the onset of, a particular condition or disease. In the context of some conditions, methods of the present invention involve "treating" the condition in terms of reducing or eliminating the occurrence of a highly undesirable and irreversible outcome of the progression of the condition but may not of itself prevent the initial occurrence of the condition. Accordingly, treatment and prevention include amelioration of the symptoms of a particular condition or preventing or otherwise reducing the risk of developing a particular condition.

As used herein the terms "effective amount" and "effective dose" include within their meaning a non-toxic but sufficient amount or dose of an agent or compound to provide the desired effect. The exact amount or dose required will vary from subject to subject depending on factors such as the species being treated, the age and general condition of the subject, the severity of the condition being treated, the particular agent being administered and the mode of administration and so forth. Thus, it is not possible to specify an exact "effective amount" or "effective dose". However, for any given case, an appropriate "effective amount" or "effective dose" may be determined by one of ordinary skill in the art using only routine experimentation.

The present invention provides a series of novel modified or chimeric relaxin polypeptides. The modified polypeptides of the invention possess different combinations of B and A chains than those present in naturally occurring relaxin polypeptides and in particular embodiments comprise a B chain sequence derived from H2 relaxin or H1 relaxin or a modified B chain sequence comprising a core amino acid sequence common to the B chain of H2 and H1 relaxins. The 23 amino acid sequence VIKLCGRELVRAQIAICGMSTWS (SEQ ID NO:4) is common to the B chain of both H2 and H1 relaxin. Accordingly, in one aspect the invention provides a modified relaxin polypeptide comprising a B chain comprising the sequence as set forth in SEQ ID NO:4 or a portion thereof. By way of example, the portion may comprise the amino acid sequence set forth in SEQ ID NO:3.

Further, as will be noted from the alignment of relaxin B chain sequences shown in FIG. 1, the core sequence CGR-XXX-R-XXXXX-CG, where X is any amino acid, is highly conserved. Accordingly the invention also provides a modified relaxin polypeptide comprising a B chain comprising the sequence CGR-XXX-R-XXXXX-CG. In an embodiment, the B chain comprising the sequence CGR-XXX-R-XX-I/V-XX-CG (SEQ ID NO:1).

Further embodiments of the invention contemplate modified polypeptides in which the B chain comprises the sequence XWXXXVIKLCGRELVRAQIAICGMSTWS (SEQ ID NO:5) (where X is any amino acid), $X_1X_2WX_3X_4X_4$VIKLCGRELVRAQIAICGMSTWS (SEQ ID NO:6) (where: $X_1$, if present, is D; $X_2$ is S or K; $X_3$ is M or K; and $X_4$ is an acidic residue), DSWMEEVIKLCGRELVRAQIAICGMSTWS derived from H2 relaxin (SEQ ID NO:7), or KWKDDVIKLCGRELVRAQIAICGMSTWS derived from H1 relaxin (SEQ ID NO:8), or a portion thereof.

In the modified polypeptides of the invention the A chain amino acid sequence may be derived from any other relaxin polypeptide such that the modified polypeptide is a chimeric molecule. For example, the A chain may be derived from relaxin 1, relaxin 2, relaxin 3, insulin, IGF-I, IGF-II or insulin-like peptides (INSL) 3, 4, 5 or 6. These sequences may be derived from any suitable species, but typically human. The human A chain sequences disclosed herein are: H2 relaxin A chain (SEQ ID NO:9); H1 relaxin A chain (SEQ ID NO:10);

H3 relaxin A chain (SEQ ID NO:11); INSL3 A chain (SEQ ID NO:12); INSL4 A chain (SEQ ID NO:13); INSL5 A chain (SEQ ID NO:14); INSL6 A chain (SEQ ID NO:15); insulin A chain (SEQ ID NO:16); IGF-I A chain (SEQ ID NO:17); and IGF-II A chain (SEQ ID NO:18).

In the modified polypeptides of the invention, the B and/or A chain sequence may be modified from that found in a naturally occurring relaxin molecule by any one of a number of means well known to those skilled in the art. For example the amino acid sequence may be modified by one or more amino acid insertions, deletions and/or substitutions.

As disclosed herein the present invention contemplates modified relaxin polypeptides in which the B and/or A chains possess one or more amino acid deletions, additions or substitutions in comparison with a corresponding wild-type relaxin polypeptide. Amino acid changes in relaxin polypeptides may be effected by techniques well known to those persons skilled in the relevant art. For example, amino acid changes may be effected by nucleotide replacement techniques which include the addition, deletion or substitution of nucleotides (conservative and/or non-conservative), under the proviso that the proper reading frame is maintained. A conservative substitution denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution" also includes the use of a substituted amino acid in place of an unsubstituted parent amino acid. Exemplary techniques for generating such amino acid insertion, deletion or substitution modifications include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction. Such techniques will be well known to those skilled in the art.

Polypeptides of the invention can also be further modified, for instance, by glycosylation, amidation, carboxylation, or phosphorylation, or by the creation of acid addition salts, amides, esters, in particular C-terminal esters, and N-acyl derivatives of the peptides of the invention. The polypeptides can also be further modified to create polypeptide derivatives by forming covalent or noncovalent complexes with other moieties. Covalently-bound complexes can be prepared by cross-linking the chemical moieties to functional groups on the side chains of amino acids comprising the peptides, or at the N- or C terminus. Further, the polypeptides of the invention can be conjugated to a reporter group, including, but not limited to a radiolabel, a fluorescent label, an enzyme (e.g., that catalyzes a colorimetric or fluorometric reaction), a substrate, a solid matrix, or a carrier (e.g., biotin or avidin). These are merely exemplary additional modifications that may be made to the modified polypeptides of the invention. Those skilled in the art will appreciate that further modifications may also be made so as to generate analogues of the polypeptides of the invention. By way of example only, illustrative analogues and processes for preparing the same are described in International patent application published as WO 2004/113381, the disclosure of which is incorporated herein by reference in its entirety.

Amino acid additions may also result from the fusion of a relaxin polypeptide or fragment thereof with a second polypeptide or peptide, such as a polyhistidine tag, maltose binding protein fusion, glutathione S transferase fusion, green fluorescent protein fusion, or the addition of an epitope tag such as FLAG or c-myc. Additionally, modified polypeptides of the invention may further include a relaxin C chain. Relaxin C chain amino acid sequences are known to those skilled in the art.

The present invention also contemplates fragments and variants of the polypeptides disclosed herein.

The term "fragment" refers to a polypeptide molecule that encodes a constituent or is a constituent of a polypeptide of the invention or variant thereof. Typically the fragment possesses qualitative biological activity in common with the polypeptide of which it is a constituent. The peptide fragment may be between about 5 to about 150 amino acids in length, between about 5 to about 100 amino acids in length, between about 5 to about 50 amino acids in length, or between about 5 to about 25 amino acids in length. Alternatively, the peptide fragment may be between about 5 to about 15 amino acids in length.

The term "variant" as used herein refers to substantially similar sequences. Generally, polypeptide sequence variants possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polypeptides of the invention. A homologue is typically a polypeptide from a different species but sharing substantially the same biological function or activity as the corresponding polypeptide disclosed herein.

Further, the term "variant" also includes analogues of the polypeptides of the invention, wherein the term "analogue" means a polypeptide which is a derivative of a polypeptide of the invention, which derivative comprises addition, deletion, substitution of one or more amino acids, such that the polypeptide retains substantially the same function.

Relaxin polypeptides modified at the N- and/or C-terminus by the addition, deletion or substitution of one or more amino acid residues as described above also fall within the scope of the present invention.

In accordance with the present invention relaxin polypeptides may be produced using standard techniques of recombinant DNA and molecular biology that are well known to those skilled in the art. Guidance may be obtained, for example, from standard texts such as Sambrook et al., *Molecular Cloning: A Laboratory Manual*, Cold Spring Harbor, N.Y., 1989 and Ausubel et al., *Current Protocols in Molecular Biology*, Greene Publ. Assoc. and Wiley-Intersciences, 1992. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable purification methods for relaxin polypeptides, although the skilled addressee will appreciate that the present invention is not limited by the method of purification or production used and any other method may be used to produce relaxin for use in accordance with the methods and compositions of the present invention. Relaxin peptide fragments may be produced by digestion of a polypeptide with one or more proteinases such as endoLys-C, endoArg-C, endoGlu-C and staphylococcus V8-protease. The digested peptide fragments can be purified by, for example, high performance liquid chromatographic (HPLC) techniques.

The purification of relaxin polypeptides of the invention may be scaled-up for large-scale production purposes. For this purpose a range of techniques well known to those skilled in the art are available.

Relaxin polypeptides of the present invention, as well as fragments and variants thereof, may also be synthesised by standard methods of liquid or solid phase chemistry well known to those of ordinary skill in the art. For example such molecules may be synthesised following the solid phase chemistry procedures of Steward and Young (Steward, J. M. & Young, J. D., Solid Phase Peptide Synthesis. (2nd Edn.) Pierce Chemical Co., Illinois, USA (1984).

In general, such a synthesis method comprises the sequential addition of one or more amino acids or suitably protected amino acids to a growing peptide chain. Typically, either the amino or carboxyl group of the first amino acid is protected by a suitable protecting group. The protected amino acid is then either attached to an inert solid support or utilised in solution by adding the next amino acid in the sequence having the complimentary (amino or carboxyl) group suitably protected and under conditions suitable for forming the amide linkage. The protecting group is then removed from this newly added amino acid residue and the next (protected) amino acid is added, and so forth. After all the desired amino acids have been linked, any remaining protecting groups, and if necessary any solid support, is removed sequentially or concurrently to produce the final polypeptide.

Embodiments of the present invention provide isolated polynucleotides encoding relaxin polypeptides as described above, and variants and fragments of such polynucleotides.

Those skilled in the art will appreciate that heterologous expression of polypeptides may be improved by optimising the codons for the particular species in which the relaxin polypeptide is to be expressed. Accordingly, polynucleotides encoding relaxin polypeptides of the invention may be codon-optimised for expression in a particular species.

Fragments of polynucleotides of the invention are also contemplated. The term "fragment" refers to a nucleic acid molecule that encodes a constituent or is a constituent of a polynucleotide of the invention. Fragments of a polynucleotide, do not necessarily need to encode polypeptides which retain biological activity. Rather the fragment may, for example, be useful as a hybridization probe or PCR primer. The fragment may be derived from a polynucleotide of the invention or alternatively may be synthesized by some other means, for example chemical synthesis. Polynucleotides of the invention and fragments thereof may also be used in the production of antisense molecules using techniques known to those skilled in the art.

In particular embodiments, polynucleotides of the invention may be cloned into a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences.

The present invention also provides antibodies that selectively bind to the relaxin polypeptides of the present invention, as well as fragments and analogues thereof. Suitable antibodies include, but are not limited to polyclonal, monoclonal, chimeric, humanised, single chain, Fab fragments, and an Fab expression library. Antibodies of the present invention may act as agonists or antagonists of relaxin polypeptides, or fragments or analogues thereof.

Methods for the generation of suitable antibodies will be readily appreciated by those skilled in the art. For example, an anti-relaxin monoclonal antibody, typically containing Fab portions, may be prepared using the hybridoma technology described in Antibodies-A Laboratory Manual, Harlow and Lane, eds., Cold Spring Harbor Laboratory, N.Y. (1988).

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti-relaxin antibody. Alternatively, the anti-relaxin antibody may be detected by virtue of its binding with a secondary antibody or reagent which is appropriately labelled. A variety of methods are known in the art for detecting binding in an immunoassay and are within the scope of the present invention.

Relaxin polypeptides and polynucleotides of the invention may be useful as therapeutic agents. These molecules find use, for example, in treating or preventing a disease or condition in a subject, by administering a therapeutically effective amount of such a molecule to the subject. Agonists and antagonists of relaxin polypeptides of the invention, including anti-relaxin antibodies, may also be useful as therapeutic agents. Accordingly, the present invention also contemplates methods of treatment using such agonists and antagonists and pharmaceutical compositions comprising the same.

By way of example only, modified polypeptides of the invention, polynucleotides encoding the same and compositions comprising such polypeptides or polynucleotides may be used in the treatment or prophylaxis of cardiovascular, renal and neurological diseases or other diseases or conditions associated with aberrant relaxin expression or activity.

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralised or distilled water; saline solution; vegetable based oils such as peanut oil, safflower oil, olive oil, cottonseed oil, maize oil, sesame oils such as peanut oil, safflower oil, olive oil, cottonseed oil, maize oil, sesame oil, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include, Ringer's solution, isotonic saline, phosphate buffered saline, ethanol and 1,2 propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatine and lecithin. In addition these oral formulations may contain suitable flavouring and colourings agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilisers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

For the purposes of the present invention molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to about 500 mg/m$^2$. Generally, an effective dosage is expected to be in the range of about 25 to about 500 mg/m$^2$, preferably about 25 to about 350 mg/m$^2$, more preferably about 25 to about 300 mg/m$^2$, still more preferably about 25 to about 250 mg/m$^2$, even more preferably about 50 to about 250 mg/m$^2$, and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as, the number of doses of the composition given per day for a defined number of days, can be ascertained by those skilled in the art using conventional course of treatment determination tests.

Embodiments of the invention also contemplate the administration of a polynucleotide encoding a modified relaxin polypeptide of the invention. In such situations the polynucleotide is typically operably linked to a promoter such that the appropriate polypeptide sequence is produced following administration of the polynucleotide to the subject. The polynucleotide may be administered to subjects in a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

Those skilled in the art will appreciate that in accordance with the methods of the present invention relaxin polypeptides of the invention may be administered alone or in conjunction with one or more additional agents. Additionally, the present invention contemplates combination therapy using relaxin polypeptides of the invention in conjunction with other therapeutic approaches to the treatment of diseases and disorders. For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

The reference in this specification to any prior publication (or information derived from it), or to any matter which is known, is not, and should not be taken as an acknowledgment or admission or any form of suggestion that that prior publication (or information derived from it) or known matter forms part of the common general knowledge in the field of endeavour to which this specification relates.

The present invention will now be described with reference to the following specific examples, which should not be construed as in any way limiting the scope of the invention.

EXAMPLES

Example 1

Chimeric Relaxin Polypeptide Construction

For the purposes of the present study, a number of chimeric relaxin polypeptides were constructed, each comprising the human H2 relaxin B chain (SEQ ID NO:7) linked to an A chain from a different member of the relaxin superfamily. The chimeric polypeptides constructed were as follows: H2 B chain/H1 relaxin A chain (H2-B/H1-A); H2 B chain/H3 relaxin A chain (H2-B/H3-A); H2 B chain/INSL3 A chain (H2-B/INSL3-A); H2 B chain/INSL5 A chain (H2-B/INSL5-A); and H2 B chain/insulin A chain (H2-B/INSL-A).

The chimeric polypeptides were constructed in accordance with the following protocol, which for the purposes of exemplification only, details construction of the H2-B/H1-A chimeric polypeptide.

Solid-Phase Peptide Synthesis

The selectively S-protected H1 relaxin A- and H2 relaxin B-chains were assembled as their C-terminal acids by the continuous flow Fmoc solid phase synthesis methodology, essentially as previously described (Bathgate et al., 2006, *Biochemistry* 45:1043-1053). The solid support was appropriately Fmoc-Cys(Acm)-NovaSyn TGT (Novabiochem) for the A-chain and Fmoc-Ser-PAC-PEG-PS-terminal amino acid-linked PAC-PEG-PS (PerSeptive Biosystems, USA) and HBTU-activated Fmoc-amino acids were used throughout. Amino acid side chain protection was afforded by the following: Arg, Pbf; Gln, Trt; Asp and Glu, O-Bu$^t$; Tyr, Bu$^t$; His, Trt; Lys, Boc; Ser, Bu$^t$; and Trp, Boc. For the A-chain peptide, S-protection was afforded by Trt (Cys$^{10,15}$), Acm (Cys$^{24}$) and But (Cys$^{11}$). Residue 1 of the A-chain was coupled as pyroglutamic acid. For the B-chain, Trt (Cys$^{11}$) and Acm (Cys$^{23}$) were used. All amino acid derivatives were purchased from Auspep (Melbourne, Australia). No repeat couplings were carried out. N$^\alpha$-Fmoc deprotection was with 20% piperidine in DMF. Assembly of both the A- and B-chain peptides commenced on 0.125 and 0.10 mmol scales respectively using a 4-fold excess of activated amino acid and 30 min coupling times. After acylation and deprotection of the final residues, cleavage from the solid supports and side chain deprotection was achieved by a 2.5-h treatment of the two separate peptide-resins with trifluoroacetic acid (TFA) and, for the B-chain, in the presence of phenol, thioanisole, ethanedithiol and water (82.5/5/5/2.5/5, v/v) with a few drops triethylsilane (TES). For the A-chain, cleavage was TFA in the presence of ethanedithiol, water and TES (95/2/2/1). The resulting crude peptides were subjected to preparative reversed-phase high performance liquid chromatography (RP-HPLC) on a Vydac C18 column (Hesperia, USA) using a 1%/min gradient of CH$_3$CN in 0.1% aqueous TFA.

A-Chain Intramolecular Disulfide Oxidation

Crude cleaved [Cys$^{10,15}$(S-thiol), Cys$^{11}$(But), Cys$^{24}$(Acm)] A-chain (976 mgs, 335 µmol) was dissolved in 0.1 M Gly.NaOH, pH 8.5, (2.5 L) and to this was added 1 mM 2-dipyridyl disulfide (DPDS) in MeOH (214 ml, 214 µmol) (as per Maruyama et al., 1999, *Peptides* 20:881-884). Oxidation was completed after 2 hours as monitored by analytical RP-HPLC. The solution was acidified by addition of neat TFA and then the peptide isolated by preparative RP-HPLC and subsequent freezedrying to give 168.2 mgs (59.2 µmol, 27%) of purified [Cys$^{11}$(Acm), Cys$^{24}$(But)]-A-chain.

[Cys$^{11}$(Pyr), Cys$^{24}$(Acm)]A-Chain

Intramolecular disulfide bonded [Cys$^{11}$(But), Cys$^{24}$(Acm)]-A-chain (168 mg, 59.1 µmol) was converted to the Cys$^{24}$ S-pyridinylsulfenyl form by treatment with DPDS (as per Maruyama et al., 1992, *J Protein Chem* 11:13-20) in neat TFA (5.0 ml) containing thioanisole (0.5 ml) chilled to ≤0° C., before 5.0 ml TFMSA/TFA (1:5 v/v) was added and stirred for 30 minutes maintaining the temperature at or below 0° C. The peptide was then precipitated in ether and the pellet suspended in 6MGdHCl, pH 8.0 for purification. The target peptide was isolated by preparative RP-HPLC to give 148.6 mg (86.8%).

Combination of [Cys$^{11}$(Pyr), Cys$^{24}$(Acm)]A-Chain with [Cys$^{11}$(S-Thiol), Cys$^{23}$(Acm)]B-Chain A-chain peptide (120.9 mg, 41.8 µmol) was dissolved in 0.1 mM NH$_4$HCO$_3$ or 8M GdHCl, pH 8.5 (7.0 ml) and added to crude B-chain (153.0 mg, 37.4 µmol) in the same buffer (11 ml). The mixture was stirred vigorously at 37° C. and the reaction monitored by analytical RP-HPLC. After 30 minutes (or 24 hours if using the GdHCl buffer), the reaction was terminated by addition of glacial acetic acid, and the target product isolated by preparative RP-HPLC to give 57.6 mg (8.4 µmol, 10.5%).

Purification of H2-B/H1-A

The [Cys$^{24}$(Acm)]A-chain/[Cys$^{23}$(Acm)] B-chain (57.6 mg, 8.4 µmol) was dissolved in glacial acetic acid (26.6 ml) and 80 mM HCl and to this was added dropwise 25.2 ml of 20 mM iodine/acetic acid (0.50 mmol). After 1 hour, the reaction was stopped by addition of 25.2 ml of 20 mM ascorbic acid. Preparative RP-HPLC, as described above, was then used to isolate and purify the product (23.7 mg, 3.50 μmol, 42.0% yield, 4.4% overall relative to starting crude B-chain).

Characterization of H2-B/H1-A

The purity of the synthetic hybrid relaxin peptide was assessed by analytical RP-HPLC, and matrix-assisted laser desorption time of flight (MALDITOF) mass spectrometry using a Bruker Autoflex II instrument (Bremen, Germany) in the linear mode at 19.5 kV. Peptide quantitation was determined by amino acid analysis of a 24 hour acid hydrolyzate using a GBC instrument (Melbourne, Australia).

Example 2

Biological Activity of Chimeric Relaxin Polypeptides

Each of H1, H2 and H3 relaxins bind specifically to cell surface relaxin receptors and stimulate intracellular cAMP production in a dose-dependent manner. The ability of relaxins to stimulate cAMP production is typically used as an indicator of relaxin biological activity.

In the present study the inventors investigated the ability of chimeric polypeptides generated herein (see Example 1) to stimulate cAMP production in cells expressing either the LGR7 or LGR8 receptor. Binding to the GPCR135 (RXFP3) and GPCR142 (RXFP4) receptors is governed by specific residues in the relaxin B chain that are not present in the B chain of H2 relaxin. Thus, none of the chimeric polypeptides exemplified herein will bind or activate these receptors.

Figure 6:
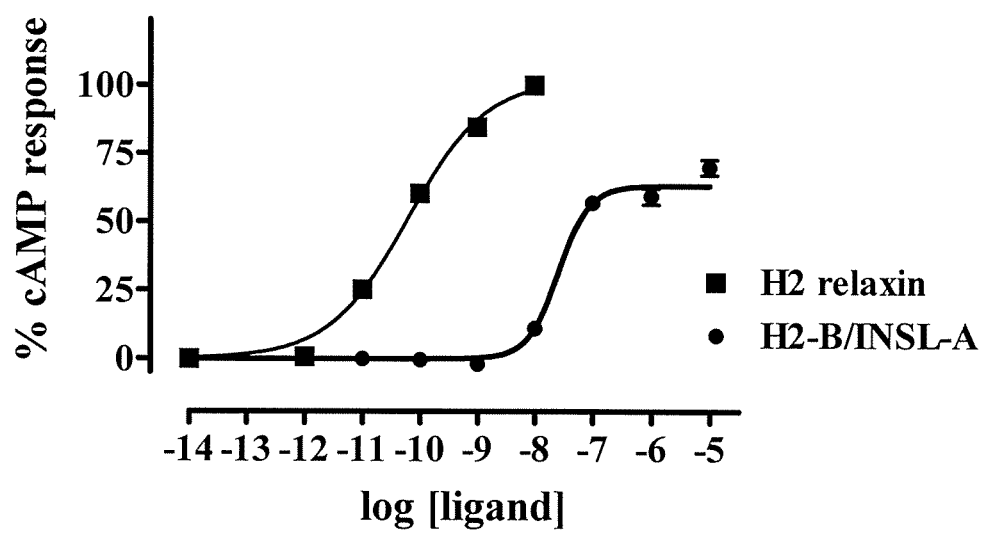
FIG. 6. Stimulation of cAMP by human relaxin 2 (H2) (filled squares) and a modified polypeptide of the invention comprising the H2 B chain and the INSL A chain (filled circles) in cells expressing the LGR7 (RXFP1) receptor.
Figure 7:
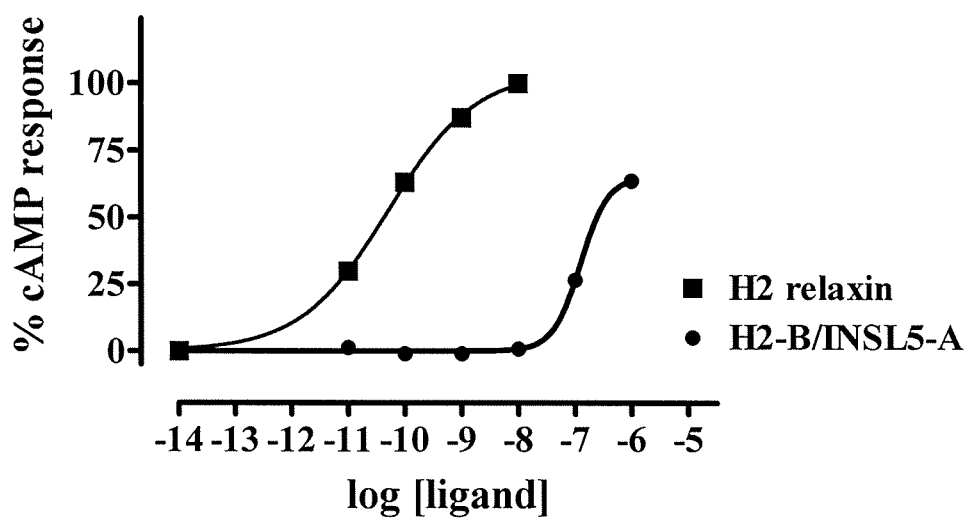
FIG. 7. Stimulation of cAMP by human relaxin 2 (H2) (filled squares) and a modified polypeptide of the invention comprising the H2 B chain and the INSL5 A chain (filled circles) in cells expressing the LGR7 (RXFP1) receptor.

Receptor cAMP signaling was assessed using a cAMP reporter gene assay. HEK-293T cells in 96-well plates were co-transfected with receptors (either LGR7 or LGR8) and a pCRE-β-galactosidase reporter plasmid (courtesy of Dr R Cone, Disorders Oregon Health and Science University, USA) to assess the cAMP signaling response to H2 relaxin and chimeric peptides. Transfected cells were incubated with increasing concentrations of peptides for 6 hrs after which the media was aspirated and the cells frozen at −80° C. overnight. The amount of cAMP-driven β-galactosidase expression in each well was determined by incubating the cells in 25 μl of lysis buffer (10 mM $Na_2HPO_4$, pH 8.0, 0.2 mM $MgSO_4$, 0.01 mM $MnCl_2$) for 10 minutes, 100 μl of assay buffer (100 mM $Na_2HPO_4$, pH 8.0, 2 mM $MgSO_4$, 0.1 mM $MnCl_2$, 0.5% Triton X-100, 40 mM B-mercaptoethanol) for a further 10 minutes before 25 μL of enzyme substrate solution (1 mg/ml chlorophenol red B-D galactopyranoside (Roche) in 100 mM $Na_2HPO_4$, pH 8.0, 2 mM $MgSO_4$, 0.1 mM $MnCl_2$) was added to each well and the plate incubated for 3 h or overnight. The absorbance of each well was determined at 570 nm using a Ceres UV900C plate reader (Bio-Tek Instruments, Vermont, USA).

cAMP signalling induced by chimeric relaxin polypeptides was determined and compared with signalling induced by H2 relaxin. Results are illustrated in FIG. 3 (H2-B/H3-A in LGR7-expressing cells (A) and LGR8-expressing cells (B)), FIG. 4 (H2-B/H1-A in LGR7-expressing cells (A) and LGR8-expressing cells (B)), FIG. 5 (H2-B/INSL3-A in LGR7-expressing cells), FIG. 6 (H2-B/INSL-A in LGR7-expressing cells) and FIG. 7 (H2-B/INSL5-A in LGR7-expressing cells). All experiments were repeated at least three times with triplicate determinations within each assay. Results are plotted as mean±S.E.M of percent normalized response compared to the maximum H2 relaxin response.

Example 3

Receptor Binding Affinities of Chimeric Relaxin Polypeptides

Whole cell [125I]-labelled H2 relaxin competition binding assays were performed as previously described (Sudo et al., 2003, *J Biol Chem* 278:7855-7862). Briefly, HEK293T cells were plated out into 24-well plates (450,000 cells per well) or 48-well plates (225,000 cells per well), and transfected with pcDNA3.1/zeo plasmid containing the receptor of interest the following day as described above in Example 2. 24 hours after transfection, competition binding assays were performed with 100 pM of [125I]-H2 relaxin in the absence or presence of increasing concentrations of unlabelled peptides. Non-specific binding was determined by addition of excess unlabelled relaxin (500 nM). Data were analysed using GraphPad Prism.

Table 1 shows the binding affinities ($pK_i$) of chimeric relaxin polypeptides to the LGR7 receptor and summarises the ability of the chimeric polypeptides to stimulate cAMP accumulation ($pEC_{50}$) (see Example 2) in LGR7- and LGR8-expressing cells. Data are presented as the mean±S.E.M. of at least 1 experiment (number performed shown in parentheses in Table 1) performed in triplicate.

TABLE 1

Receptor binding ($pK_i$) and cAMP stimulation ($pEC_{50}$) for modified relaxin polypeptides comprising the H2 B chain

| Ligand | 125I-relaxin LGR7 $pK_i$ | LGR7 cAMP $pEC_{50}$ | LGR8 cAMP $pEC_{50}$ |
|---|---|---|---|
| H3 (wild-type; A + B chain) | 7.88 ± 0.04 (3) | 9.36 ± 0.21 (4)* | N/A |
| H2 (wild-type; A + B chain) | 9.03 ± 0.09 (3) | 10.35 ± 0.04 (5) | 9.13 ± 0.06 (3) |
| H2-B/H1-A | 7.82 ± 0.21 (3)* | 8.99 ± 0.25 (5)** | 7.91 ± 0.36 (3)* |
| H2-B/H3-A | 6.80 ± 0.43 (3)** | 8.10 ± 0.14 (4)** | 5.34 ± 0.23 (3)** |
| H2-B/INSL3-A | 6.21 ± 0.04 (3)** | <6(3) | >6(3) |
| H2-B/INSL5-A | 5.31 ± 0.29 (3)** | 6.37 ± 0.09 (3)** | ND |
| H2-B/INSL-A | 5.88 ± 0.27 (3)** | 7.23 ± 0.19 (3)** | ND |

*$p < 0.05$ vs H2 relaxin;
**$p < 0.001$ vs H2 relaxin;
ND-not determined;
N/A-not applicable

The invention claimed is:

1. A relaxin polypeptide comprising at least an A and a B chain, wherein the B chain comprises the amino acid sequence $X_1X_2WX_3X_4X_4VIKLCGRELVRAQIAICGMSTWS$ (SEQ ID NO:6), where: $X_1$ (if present) is D; $X_2$ is S or K; $X_3$ is M or K; and $X_4$ is an acidic residue, and wherein the A chain is a relaxin 3, insulin, IGF-I, IGF-II or insulin-like peptide (INSL) 3, 4, 5 or 6 A chain.

2. The relaxin polypeptide according to claim 1 wherein $X_4$ is D or E.

3. The relaxin polypeptide according to claim 1 comprising the H2 relaxin B chain sequence DSWMEEVIKL-CGRELVRAQIAICGMSTWS (SEQ ID NO:7).

4. The-modified relaxin polypeptide according to claim 1 wherein the A chain comprises an amino acid sequence as set forth in any one of SEQ ID Nos:11 to 18.

5. A pharmaceutical composition comprising a polypeptide according to claim 4, optionally together with one or more pharmaceutically acceptable carriers, excipients or diluents.

6. A polynucleotide encoding a polypeptide according to claim 1.

7. A pharmaceutical composition comprising a polynucleotide according to claim 6, optionally together with one or more pharmaceutically acceptable carriers, excipients or diluents.

8. A pharmaceutical composition comprising a polypeptide according to claim 1, optionally together with one or more pharmaceutically acceptable carriers, excipients or diluents.

9. The relaxin polypeptide according to claim 1 wherein the A chain comprises an amino acid sequence as set forth in any one of SEQ ID NOs:10 to 18.

10. A relaxin polypeptide comprising at least an A and a B chain, wherein the B chain comprises the amino acid sequence DSWMEEVIKLCGRELVRAQIAICGMSTWS (SEQ ID NO:7), and wherein the A chain is a relaxin 3, relaxin 1, insulin, IGF-I, IGF-II or insulin-like peptide (INSL) 3, 4, 5 or 6 A chain.

11. A polynucleotide encoding a polypeptide according to claim 10.

12. A pharmaceutical composition comprising a polynucleotide according to claim 11, optionally together with one or more pharmaceutically acceptable carriers, excipients or diluents.

13. A pharmaceutical composition comprising a polypeptide according to claim 10, optionally together with one or more pharmaceutically acceptable carriers, excipients or diluents.

\* \* \* \* \*

SEQUENCE LISTING

<160> NUMBER OF SEQ ID NOS: 18

<210> SEQ ID NO 1
<211> LENGTH: 14
<212> TYPE: PRT
<213> ORGANISM: Artificial

```
<220> FEATURE:
<223> OTHER INFORMATION: Synthetic sequence
<220> FEATURE:
<221> NAME/KEY: MISC_FEATURE
<222> LOCATION: (4)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa = I or V
<220> FEATURE:
<221> NAME/KEY: MISC_FEATURE
<222> LOCATION: (11)..(12)
<223> OTHER INFORMATION: Xaa can be any naturally occurring amino acid

<400> SEQUENCE: 1

Cys Gly Arg Xaa Xaa Xaa Arg Xaa Xaa Xaa Xaa Cys Gly
1               5                   10

<210> SEQ ID NO 2
<211> LENGTH: 14
<212> TYPE: PRT
<213> ORGANISM: Artificial
<220> FEATURE:
<223> OTHER INFORMATION: Synthetic sequence
<220> FEATURE:
<221> NAME/KEY: MISC_FEATURE
<222> LOCATION: (4)..(6)
<223> OTHER INFORMATION: Xaa can be any naturally occurring amino acid
<220> FEATURE:
<221> NAME/KEY: MISC_FEATURE
<222> LOCATION: (8)..(9)
<223> OTHER INFORMATION: Xaa can be any naturally occurring amino acid
<220> FEATURE:
<221> NAME/KEY: MISC_FEATURE
<222> LOCATION: (11)..(12)
<223> OTHER INFORMATION: Xaa can be any naturally occurring amino acid

<400> SEQUENCE: 2

Cys Gly Arg Xaa Xaa Xaa Arg Xaa Xaa Ile Xaa Xaa Cys Gly
1               5                   10

<210> SEQ ID NO 3
<211> LENGTH: 15
<212> TYPE: PRT
<213> ORGANISM: Homo sapiens

<400> SEQUENCE: 3

Lys Leu Cys Gly Arg Glu Leu Val Arg Ala Gln Ile Ala Ile Cys
1               5                   10                  15

<210> SEQ ID NO 4
<211> LENGTH: 23
<212> TYPE: PRT
<213> ORGANISM: Homo sapiens

<400> SEQUENCE: 4

Val Ile Lys Leu Cys Gly Arg Glu Leu Val Arg Ala Gln Ile Ala Ile
1               5                   10                  15

Cys Gly Met Ser Thr Trp Ser
            20

<210> SEQ ID NO 5
<211> LENGTH: 28
<212> TYPE: PRT
<213> ORGANISM: Artificial
```

```
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (3)..(5)
<223> OTHER INFORMATION: Xaa can be any naturally occurring amino acid

<400> SEQUENCE: 5

Xaa Trp Xaa Xaa Xaa Val Ile Lys Leu Cys Gly Arg Glu Leu Val Arg
1               5                   10                  15

Ala Gln Ile Ala Ile Cys Gly Met Ser Thr Trp Ser
            20                  25

<210> SEQ ID NO 6
<211> LENGTH: 29
<212> TYPE: PRT
<213> ORGANISM: Artificial
<220> FEATURE:
<223> OTHER INFORMATION: Synthetic sequence
<220> FEATURE:
<221> NAME/KEY: misc_feature
<222> LOCATION: (1)..(1)
<223> OTHER INFORMATION: Xaa = D, if present
<220> FEATURE:
<221> NAME/KEY: misc_feature
<222> LOCATION: (2)..(2)
<223> OTHER INFORMATION: Xaa = S or K
<220> FEATURE:
<221> NAME/KEY: misc_feature
<222> LOCATION: (4)..(4)
<223> OTHER INFORMATION: Xaa = M or K
<220> FEATURE:
<221> NAME/KEY: misc_feature
<222> LOCATION: (5)..(6)
<223> OTHER INFORMATION: Xaa = an acidic residue

<400> SEQUENCE: 6

Xaa Xaa Trp Xaa Xaa Xaa Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 7
<211> LENGTH: 29
<212> TYPE: PRT
<213> ORGANISM: Homo sapiens

<400> SEQUENCE: 7

Asp Ser Trp Met Glu Glu Val Ile Lys Leu Cys Gly Arg Glu Leu Val
1               5                   10                  15

Arg Ala Gln Ile Ala Ile Cys Gly Met Ser Thr Trp Ser
            20                  25

<210> SEQ ID NO 8
<211> LENGTH: 28
<212> TYPE: PRT
<213> ORGANISM: Homo sapiens

<400> SEQUENCE: 8

Lys Trp Lys Asp Asp Val Ile Lys Leu Cys Gly Arg Glu Leu Val Arg
1               5                   10                  15

Ala Gln Ile Ala Ile Cys Gly Met Ser Thr Trp Ser
            20                  25
```

```
<210> SEQ ID NO 9
<211> LENGTH: 24
<212> TYPE: PRT
<213> ORGANISM: Homo sapiens

<400> SEQUENCE: 9

Gln Leu Tyr Ser Ala Leu Ala Asn Lys Cys Cys His Val Gly Cys Thr
1               5                   10                  15

Lys Arg Ser Leu Ala Arg Phe Cys
            20

<210> SEQ ID NO 10
<211> LENGTH: 23
<212> TYPE: PRT
<213> ORGANISM: Homo sapiens

<400> SEQUENCE: 10

Pro Tyr Val Ala Leu Phe Glu Lys Cys Cys Leu Ile Gly Cys Thr Lys
1               5                   10                  15

Arg Ser Leu Ala Lys Tyr Cys
            20

<210> SEQ ID NO 11
<211> LENGTH: 24
<212> TYPE: PRT
<213> ORGANISM: Homo sapiens

<400> SEQUENCE: 11

Asp Val Leu Ala Gly Leu Ser Ser Ser Cys Cys Lys Trp Gly Cys Ser
1               5                   10                  15

Lys Ser Glu Ile Ser Ser Leu Cys
            20

<210> SEQ ID NO 12
<211> LENGTH: 26
<212> TYPE: PRT
<213> ORGANISM: Homo sapiens

<400> SEQUENCE: 12

Ala Ala Ala Thr Asn Pro Ala Arg Tyr Cys Cys Leu Ser Gly Cys Thr
1               5                   10                  15

Gln Gln Asp Leu Leu Thr Leu Cys Pro Tyr
            20                  25

<210> SEQ ID NO 13
<211> LENGTH: 20
<212> TYPE: PRT
<213> ORGANISM: Homo sapiens

<400> SEQUENCE: 13

Phe Asp Pro Phe Cys Cys Glu Val Ile Cys Asp Asp Gly Thr Ser Val
1               5                   10                  15

Lys Leu Cys Thr
            20

<210> SEQ ID NO 14
<211> LENGTH: 20
<212> TYPE: PRT
<213> ORGANISM: Homo sapiens

<400> SEQUENCE: 14

Asp Leu Gln Thr Leu Cys Cys Thr Asp Gly Cys Ser Met Thr Asp Leu
```

```
                1               5                   10                  15
Ser Ala Leu Cys
            20

<210> SEQ ID NO 15
<211> LENGTH: 31
<212> TYPE: PRT
<213> ORGANISM: Homo sapiens

<400> SEQUENCE: 15

Gly Tyr Ser Glu Lys Cys Cys Leu Thr Gly Cys Thr Lys Glu Glu Leu
1               5                   10                  15

Ser Ile Ala Cys Leu Pro Tyr Ile Asp Phe Lys Arg Leu Lys Glu
            20                  25                  30

<210> SEQ ID NO 16
<211> LENGTH: 21
<212> TYPE: PRT
<213> ORGANISM: Homo sapiens

<400> SEQUENCE: 16

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 17
<211> LENGTH: 25
<212> TYPE: PRT
<213> ORGANISM: Homo sapiens

<400> SEQUENCE: 17

Ala Pro Gln Thr Gly Ile Val Asp Glu Cys Cys Phe Arg Ser Cys Asp
1               5                   10                  15

Leu Arg Arg Leu Glu Met Tyr Cys Ala
            20                  25

<210> SEQ ID NO 18
<211> LENGTH: 25
<212> TYPE: PRT
<213> ORGANISM: Homo sapiens

<400> SEQUENCE: 18

Arg Arg Ser Arg Gly Ile Val Glu Glu Cys Cys Phe Arg Ser Cys Asp
1               5                   10                  15

Leu Ala Leu Leu Glu Thr Leu Cys Ala
            20                  25
```